US009226842B2

(12) United States Patent  
Sellitto

(10) Patent No.: US 9,226,842 B2  
(45) Date of Patent: Jan. 5, 2016

(54) SOCK WITH INTEGRALLY KNIT SUPPORT

(71) Applicant: RICHTER INTERNATIONAL LTD., Scarborough (CA)

(72) Inventor: Peter Sellitto, Scarborough (CA)

(73) Assignee: RICHTER INTERNATIONAL LTD., Scarborough, ON (CA)

( * ) Notice: Subject to any disclaimer, the term of this patent is extended or adjusted under 35 U.S.C. 154(b) by 214 days.

(21) Appl. No.: 13/840,844

(22) Filed: Mar. 15, 2013

(65) Prior Publication Data

US 2014/0276321 A1 Sep. 18, 2014

(51) Int. Cl.
*A61F 13/00* (2006.01)
*A61F 5/01* (2006.01)
*A41B 11/00* (2006.01)
*A41B 11/12* (2006.01)
*A61F 5/14* (2006.01)

(52) U.S. Cl.
CPC ............. *A61F 5/0127* (2013.01); *A41B 11/003* (2013.01); *A41B 11/12* (2013.01); *A61F 5/0111* (2013.01); *A61F 5/14* (2013.01)

(58) Field of Classification Search
CPC ...... A61F 13/00; A61F 13/066; A61F 13/065

USPC ........... 602/65, 66, 60, 62, 27–29; 2/239–242  
See application file for complete search history.

(56) References Cited

U.S. PATENT DOCUMENTS

| 2,676,474 | A  | * | 4/1954  | Bouthillette et al. | ........... 66/179 |
| 6,805,681 | B2 | * | 10/2004 | Yokoyama | ....................... 602/65 |
| 7,441,419 | B1 | * | 10/2008 | Dollyhite et al. | ........... 66/178 A |
| 2009/0288451 | A1 | * | 11/2009 | Yokoyama | ....................... 66/185 |

FOREIGN PATENT DOCUMENTS

FR 2749024 A1 * 11/1997

* cited by examiner

*Primary Examiner* — Kim M Lewis  
(74) *Attorney, Agent, or Firm* — Lynn C. Schumaker; Hill & Schumacher

(57) ABSTRACT

A support sock having a support structure integrally knit therewith. The sock has a toe area, an ankle area, and an intermediate area for covering a wearer's instep, ball and sole. The integrally knit support structure has an arch wrap defining at least a portion of the intermediate area. The integrally knit support also includes an upper and/or lower support band for assisting in the arch wrap. The upper support band bridges between the proximal end of the arch wrap and the ankle area. The lower support band extends from the distal end of the arch wrap.

18 Claims, 3 Drawing Sheets

SOCK WITH INTEGRALLY KNIT SUPPORT

FIELD

The present disclosure relates to socks, and in particular, socks having a support structure integrally knit therewith.

BACKGROUND

There are a number of over-the-counter arch supports and supportive insoles available for providing or improving support for the arches of the feet.

Custom-made orthotics are also available, although they are much more expensive.

Alternatively, the provision of arch support can also be done by wrapping a separate elastic bandage around the foot. Wrapping of the bandage, however, may prove uncomfortable if wrapped too tightly, or not so effective if wrapped too loosely. There may also be an element of discomfort in that the wearer's existing footwear may not have enough room to accommodate an additional thickness of the bandage.

As a more accessible and convenient option, attempts have been made to attach or incorporate arch support bands or pads into socks. Being one of the basic commodities of everyday life, socks provide a convenient framework into which support means can be incorporated, by way of sewing or knitting. Despite the inherent convenience, socks with an integrally formed arch bands or pads have some drawbacks in that they do not necessarily deliver sufficient or adequate level of support.

Therefore, it would be advantageous to provide socks with improved support.

SUMMARY

Socks having a support structure are disclosed herein.

The embodiments of the present disclosure provide a support sock which has an integrally knit support structure. The sock also has a toe area, an ankle area, and an intermediate area for covering a wearer's instep, ball and sole.

According to one aspect, the integrally knit support structure may include an arch wrap, an upper support band and a lower support band. The arch wrap defines at least a portion of the intermediate area. The arch wrap has a proximal end facing toward the ankle area and a distal end facing toward the toe area. The upper support band bridges between the proximal end of the arch wrap and the ankle area, and the lower support band extends from the distal end of the arch wrap.

According to another aspect, the integrally knit support structure may include an arch wrap, and one of an upper support band and a lower support band.

In one embodiment, the upper support band extends from the proximal end of the arch wrap toward the ankle area, encircles the ankle area, and extends back to the proximal of the arch wrap.

In one example, the upper support band may have an inverted U-shape. In another example, the upper support band may have a generally loop shape.

The lower support band may be dimensioned to cover at least a portion of the instep of the wearer, and/or at least a portion of the ball of the wearer. In one example, the lower support band may be dimensioned to cover a substantial portion of the ball.

According to the present disclosure, the arch wrap is configured for stretching in a radial direction.

The arch wrap may have a knit construction of a repeating two-wale pattern, where the first wale includes knit and float stitches, and the second wale include knit stitches.

In a preferred embodiment, the upper and lower support bands may comprise reinforcement yarns. The reinforcement yarns may include 70 denier nylon. In one embodiment, the upper and lower support bands may have diamond patterns.

According to one aspect, the support sock may include a leg area. In one embodiment, the leg area may have an elasticity of gradual compression.

A further understanding of the functional and advantageous aspects of the disclosure can be realized by reference to the following detailed description and drawings.

BRIEF DESCRIPTION OF THE DRAWINGS

The embodiments of the disclosure will now be described, by way of example only, with reference to the accompanying drawings, in which.

A further understanding of the functional and advantageous aspects of the disclosure can be realized by reference to the following detailed description and drawings.

DETAILED DESCRIPTION

Embodiments described herein provide socks having a support structure integrally knit therewith. The support structure of the present disclosure includes an arch wrap configured for supporting and lifting the arch of a wearer. The support structure also includes at least one support band configured for assisting the lifting and supporting effect of the arch wrap.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the term "exemplary" means "serving as an example, instance, or illustration," and should not be construed as preferred or advantageous over other configurations disclosed herein.

The selected embodiments as described below are directed to a sock having a support structure integrally knit therewith. The embodiments of the present disclosure provide improved support for the feet of a wearer, in particular, the arch areas.

Figure 1:
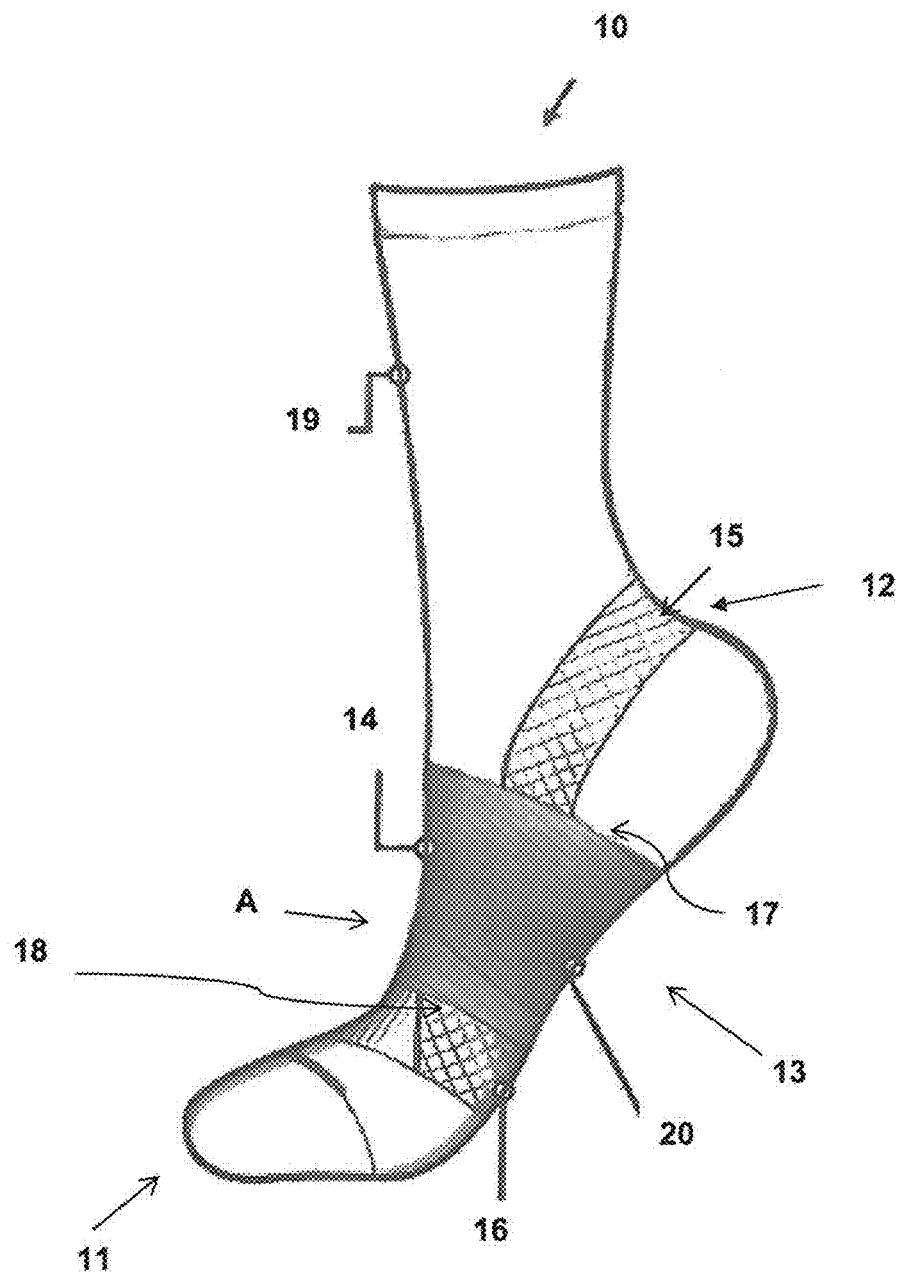
FIG. 1 is an elevation side view of one embodiment of the sock according to the present disclosure.

Referring to FIG. 1, a support sock having an integrally knit support structure is shown at 10. The sock 10 has a toe area 11, an ankle area 12, and an intermediate area 13. The intermediate area 13 covers at least portions of the instep, ball, and sole of the wearer.

In the exemplary embodiment shown in FIG. 1, the support sock 10 has an arch wrap 14 and two support bands, namely, the upper support band 15 and the lower support band 16.

The arch wrap 14 defines at least a portion of the intermediate area 13. The arch wrap 14 has a proximal end 17 facing toward the ankle area 12 and a distal end 18 facing toward the toe area 11. In the present embodiment, the arch wrap 14 is configured for stretching in a radial direction. In one preferred embodiment, the arch wrap 14 has a knit construction of a repeating two-wale pattern.

Figure 2:
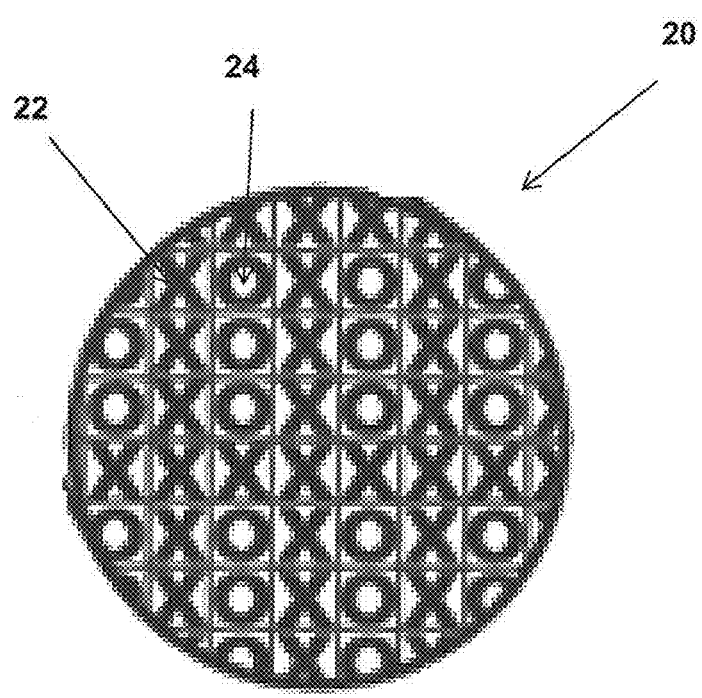
FIG. 2 is a diagram of a knit construction of an arch wrap of the sock shown in FIG. 1.

Referring to FIG. 2, the repeating two-wale pattern is shown at 20. In this embodiment, the first wale comprises knit stitches 22 and float stitches 24, and a second wale consists of knit stitches 22 only. The knit construction 20 enables the arch wrap 14 to stretch in a radial direction, while limiting the migration of stretch in an axial direction. The arch wrap 14 helps lift and support the arch in place, thereby providing improved support to the arch of the wearer.

The support structure according to the present disclosure also includes at least one support band configured for assisting in the lifting and supporting effect of the arch wrap 14.

The embodiment shown in FIG. 1 illustrates the support sock 10 having two support bands. The upper support band 15 extends from the proximal end 17 of the arch wrap 14, and continues to the ankle area 12. The upper support band 15 then encircles the arch area 12, and returns to the proximal end 17 of the arch wrap 14.

As shown in FIG. 1, the upper support band 15 may have an inverted U-shape. However, the shape of the upper support band is not restricted to the embodiment shown in FIG. 1, and any other shapes may be used for the upper support band.

Figure 3:
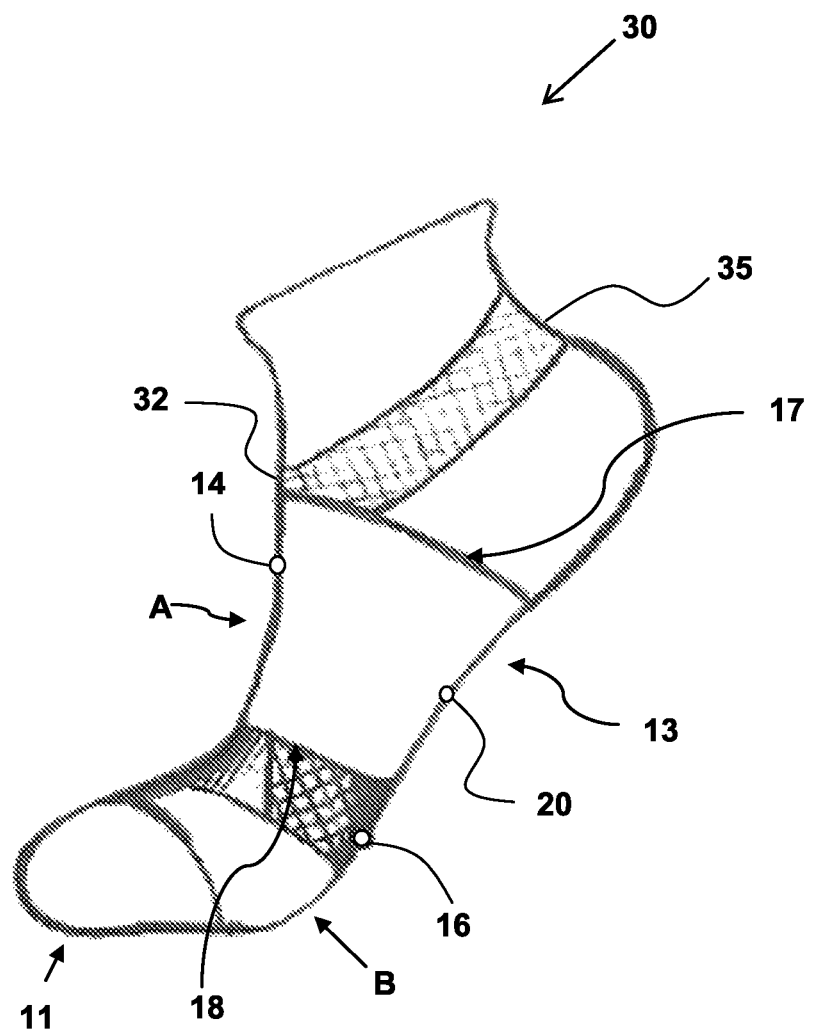
FIG. 3 is an elevation side view of a sock similar to FIG. 1, but showing an alternative shape of a support band.

Referring to FIG. 3, the support sock 30 is similar to the sock 10 shown in FIG. 1, but has an alternative shape of the upper support band shown at 35. In this embodiment, the upper support band 35 defines a generally loop shape, where the band 35 extending from the central area 32 of the proximal end 17 of the arch wrap 14 encircles the ankle area 12. The upper support band 35 then returns back to the central area 32 of the proximal end 17 of the arch wrap 14.

Referring to FIGS. 1 and 3, the lower support band 16 is dimensioned to cover at least a portion of the instep area A of the wearer. The lower support band 16 may be dimensioned to cover at least a portion of the ball B of the wearer. In one preferred embodiment, the lower support band 16 is dimensioned to cover a portion of the instep A as well as a substantial portion of the ball B. In another preferred embodiment, the lower support band 16 may be dimensioned to encircle the ball B of the wearer.

The support bands 15, 35 and 16 are configured to assist in the lifting and supporting effect of the arch wrap 12. To this end, the support bands may be made from reinforcement yarns.

In one embodiment, the support bands 15, 35 and 16 comprise 70 denier nylon. In one specific embodiment, the support bands 15, 35 and 16 may have diamond patterns.

In one embodiment as shown in FIG. 1, the support sock of the present disclosure may also include a leg area 19. In this embodiment, the leg area 19 may have an elasticity of gradual compression. In one example, some portion of the toe area 11, instep area A and ankle area 12 have the elasticity similar to that of the leg area 19. Alternatively, at least one of the toe area 11, instep area A and ankle area 12 have an elasticity different from that of the leg area 19.

The support sock according to the present disclosure may be of any desired length. For example, as shown in FIG. 3, the sock may be of an ankle length.

In another example, the sock may have a length that also covers at least a portion of the leg, or a knee high or thigh high. In another example, the support socks may be attached together to form stockings.

The support sock 10 and 30 according to the present disclosure provide improved support for the feet of a wearer, in particular, the arch areas. Therefore, the support sock disclosed herein may help those with plantar fasciitis. Moreover, the support bands provided at the proximal end and/or the distal end of the arch wrap assist in the supporting and lifting power of the arch wrap, and provide additional support to the feet, including the arches and ankle areas.

As used herein, the terms "comprises" and "comprising" are to be construed as being inclusive and opened rather than exclusive. Specifically, when used in this specification including the claims, the terms "comprises" and "comprising" and variations thereof mean that the specified features, steps or components are included. The terms are not to be interpreted to exclude the presence of other features, steps or components.

Furthermore, nothing in the present disclosure is to be construed as the promise of the invention.

Therefore what is claimed is:

1. A support sock having a toe area, an ankle area, and an intermediate area for covering a wearer's instep, ball and sole, the sock having an integrally knit support structure comprising:
    an arch wrap defining at least a portion of the intermediate area, said arch wrap having a proximal end facing toward the ankle area and a distal end facing toward the toe area;
    an upper support band bridging between the proximal end of the arch wrap and the ankle area; and
    a lower support band extending from the distal end of the arch wrap,
    wherein the arch wrap has a knit construction of a repeating two-wale pattern, a first wale comprising knit and float stitches, and a second wale consisting of knit stitches.

2. The support sock according to claim 1, wherein the upper support band extends from the proximal end of the arch wrap toward the ankle area, encircles the ankle area, and extends back to the proximal of the arch wrap.

3. The support sock according to claim 2, wherein the upper support band has an inverted U-shape.

4. The support sock according to claim 2, wherein the upper support band has a generally loop shape.

5. The support sock according to claim 2, further comprising a leg area.

6. The support sock according to claim 5, the leg area has an elasticity of gradual compression.

7. The support sock according to claim 1, wherein the lower support band is dimensioned to cover at least a portion of the instep of the wearer.

8. The support sock according to claim 1, wherein the lower support band is dimensioned to cover at least a portion of the ball of the wearer.

9. The support sock according to claim 1, wherein the lower support band is dimensioned to cover a portion of the instep and a substantial portion of the ball.

10. The support sock according to claim 1, wherein the arch wrap is configured for stretching in a radial direction.

11. The support sock according to claim 1, wherein the upper and lower support bands comprise reinforcement yarns.

12. The support sock according to claim 11, wherein the reinforcement yarns comprise 70 denier nylon.

13. The support sock according to claim 11, wherein upper and lower support bands have diamond patterns.

14. A support sock having a toe area, an ankle area, and an intermediate area for covering a wearer's instep, ball and sole, the sock having an integrally knit support structure comprising:

an arch wrap defining at least a portion of the intermediate area, said arch wrap having a proximal end facing toward the ankle area and a distal end facing toward the toe area; and a first support band extending from one of the proximal end and the distal end of the arch wrap;

wherein the arch wrap is configured for supporting the arch of the wearer, and the support band is configured for supporting and lifting the arch wrap, wherein the arch wrap has a knit construction of a repeating two-wale pattern, a first wale comprising knit and float stitches, and a second wale consisting of knit stitches.

15. The support sock according to claim 14, wherein the first support band extends from the proximal end of the arch wrap, and the sock further includes a second support band extending downwardly from the distal end of the arch wrap.

16. The support sock according to claim 14, wherein the first support band extends from the distal end of the arch wrap, and the sock further includes a second support band extending from the proximal end of the arch wrap.

17. The support sock according to claim 14, wherein the support band comprises reinforcement yarns.

18. The support sock according to claim 17, wherein the reinforcement yarns comprise 70 denier nylon.

* * * * *